US012570667B2

(12) United States Patent
Gulam Dastager et al.

(10) Patent No.: US 12,570,667 B2
(45) Date of Patent: Mar. 10, 2026

(54) COMPOUNDS WITH ANTIBACTERIAL AND ANTI VIRAL ACTIVITIES

(71) Applicant: COUNCIL OF SCIENTIFIC AND INDUSTRIAL RESEARCH (AN INDIAN REGISTERED BODY INCORPORATED UNDER THE REGN. OF SOC. ACT (ACT XXI OF 1860), New Delhi (IN)

(72) Inventors: Syed Gulam Dastager, Pune Maharashtra (IN); Amit Kumar Sahu, Pune Maharashtra (IN); Madhukar Shyam Said, Pune Maharashtra (IN)

(73) Assignee: COUNCIL OF SCIENTIFIC AND INDUSTRIAL RESEARCH AN INDIAN REGISTERED BODY INFORPORATED UNDER THE REGN. OF SOC. ACT (ACT XXI OF 1860), New Delhi (IN)

( * ) Notice: Subject to any disclaimer, the term of this patent is extended or adjusted under 35 U.S.C. 154(b) by 386 days.

(21) Appl. No.: 18/042,123

(22) PCT Filed: Aug. 16, 2021

(86) PCT No.: PCT/IN2021/050783

§ 371 (c)(1),
(2) Date: Feb. 17, 2023

(87) PCT Pub. No.: WO2022/038632

PCT Pub. Date: Feb. 24, 2022

(65) Prior Publication Data

US 2023/0312597 A1 Oct. 5, 2023

(30) Foreign Application Priority Data

Aug. 18, 2020 (IN) ............................. 202011035650

(51) Int. Cl.

| | |
|---|---|
| ***C07D 493/10*** | (2006.01) |
| ***A61K 31/351*** | (2006.01) |
| ***A61K 45/06*** | (2006.01) |
| ***A61P 31/04*** | (2006.01) |

(52) U.S. Cl.

CPC .......... *C07D 493/10* (2013.01); *A61K 31/351* (2013.01); *A61K 45/06* (2013.01); *A61P 31/04* (2018.01)

(58) Field of Classification Search

CPC .................................................... C07D 493/10
USPC .......................................................... 514/460
See application file for complete search history.

(56) References Cited

FOREIGN PATENT DOCUMENTS

| | | | |
|---|---|---|---|
| DE | 3811016 | A1 | 10/1989 |
| EP | 0324390 | A2 | 7/1989 |
| EP | 0358177 | A1 | 3/1990 |
| WO | WO-2012040841 | A1 | 4/2012 |
| WO | WO-2022038632 | A1 | 2/2022 |

OTHER PUBLICATIONS

Myskiw et al., Antiviral Res (2010), 88: 304-310.*
Wu et al., Chem of Nat. Comps. (2009), 45(3): 333-336.*
"International Application No. PCT/IN2021/050783, International Search Report and Written Opinion dated Nov. 26, 2021", (Nov. 26, 2021), 10 pgs.
Halabi, Najeeb, et al., "Protein Sectors: Evolutionary Units of Three-Dimensional Structure", Cell 138 (4), 774-786, Aug. 21, 2009, (Sep. 21, 2009), 774-786.
Tsukube, Hiroshi, et al., "Chiral Recognition of Asymmetric Amine Salts by Chemically Modified Polyether Antibiotics", J. Org. Chem. 1991, 56(2), 875-878, (1991), 875-878.

* cited by examiner

*Primary Examiner* — Taofiq A Solola
(74) *Attorney, Agent, or Firm* — Schwegman Lundberg & Woessner, P.A.

(57) ABSTRACT

The present invention discloses novel nigericin derivatives of general formula (I) that exhibit low toxicity and inhibition activity against gram-positive bacteria, gram-negative bacteria, and viruses. The present invention also discloses a process for preparation of the compound of the general formula (I). Further, the present invention provides pharmaceutical compositions comprising the compound of general formula (I) and methods to treat bacterial and viral infections.

11 Claims, 4 Drawing Sheets

COMPOUNDS WITH ANTIBACTERIAL AND ANTI VIRAL ACTIVITIES

PRIORITY CLAIM TO RELATED APPLICATIONS

This application is a U.S. national stage filing under 35 U.S.C. § 371 from International Application No. PCT/IN2021/050783, filed on 16 Aug. 2021, and published as WO2022/038632 on 24 Feb. 2022, which claims the benefit under 35 U.S.C. 119 to India application No. 202011035650, filed on 18 Aug. 2020, the benefit of priority of each of which is claimed herein, and which applications and publication are hereby incorporated herein by reference in their entirety.

FIELD OF THE INVENTION

The current invention relates to antibacterial and antiviral agents, particularly, the present invention discloses novel compounds of formula I and a process for the preparation of compounds of formula I. More particularly, the present invention relates to novel compounds having lower toxicity and activity against both bacteria and viruses. Additionally, the present invention relates to pharmaceutical compositions comprising the novel compounds for the treatment of bacterial and viral infections.

BACKGROUND AND PRIOR ART OF THE INVENTION

Antimicrobial resistance is increasing and received global concern as mortality due to infections caused by resistant pathogens is on an upsurge in all countries. In the European region, 33 000 deaths are annually reported due to AMR. Infants across the globe, mostly in developing countries, are affected by infections because of resistant pathogens. Therefore, the need for antimicrobial drugs is increasing day by day.

Nigericin, a polyether ionophore is widely used as an antimicrobial drug. The main feature of nigericin is its antibiotic activity, including activity against drug-resistant strains. Various studies have attributed nigericin with a broad spectrum of biological activities, including antibacterial activity against Gram-positive microorganisms and Gram-negative microorganisms, and antifungal activity. It also enhances the antifungal activity of rapamycin. Nigericin is also reported to be a potent anti-cancer compound because it selectively inhibits the growth of many cancer cells. Nigericin possesses very promising antimalarial potential because it kills the malarial parasite at a low effective concentration by disrupting the ion homeostasis. It is a potent inhibitor of viruses such as vaccinia, human immunodeficiency virus (HIV), and poliovirus; moreover, nigericin has been demonstrated to enhance the internalization of drugs.

However, even with these properties, it possesses high toxicity which limits its scope in pharmaceutical applications. The toxic effects of nigericin are cardiovascular in nature, apparently due to the ability of the compound to induce ion flux across membranes. Nigericin is also recognized as a potential threat agent in the battlefield and terrorist situations owing to high toxicity combined with relative ease of production. Studies have shown that in vivo toxicity of nigericin can affect the nervous system and can lead to neurobehavioral abnormalities and peripheral neuromuscular excitations.

Many derivatives of nigericin have been prepared in the past, but systematic efforts to diversify their complex structures to reduce their toxic level have so far been absent. The well-known derivatives of nigericin are prepared by conducting lengthy de novo synthesis using multiple reagents including metal and acids making such processes more expensive.

European patent application No EP0324390 discloses nigericin derivatives exhibiting both antibacterial and antiviral activities. The nigericin derivatives express a MIC value of 0.24 μg/ml (0.3 μM), and are prepared by a process using both metal and acids in reaction and extraction.

German patent application No DE3811016 discloses nigericin derivatives substituted on the F ring and prepared by a process using both metal and acids in reaction and extraction. The nigericin derivatives are derived from the hydroxyl (OH) group and are suitable for the treatment of both bacterial and viral diseases.

European patent application No EP0358177 discloses a medicine comprising nigericin derivatives and antifungal agents, exhibiting both antimycotic and antiviral activity.

To overcome the problem of high toxicity, there is a need for an effective molecule and a process that can diversify the complex structures to synthesize novel compounds with less toxicity. Also, ease of synthesis and cost-effectiveness has to be taken into consideration for such a process. Accordingly, the present invention provides compounds having low toxicity and substantial efficacy against viruses, gram-positive bacteria, and gram-negative bacteria.

OBJECTS OF THE INVENTION

An object of the present invention is to provide novel compounds to act against both bacteria and viruses. Another object of the invention is to provide a process for the preparation of novel compounds having low toxicity and activity against both gram-positive bacteria and gram-negative bacteria, and viruses.

It is yet another object of the present invention to provide a pharmaceutical composition comprising the novel compounds that can act as antibacterial and anti viral agents.

SUMMARY OF THE INVENTION

Accordingly, the present invention discloses a compound of general formula I,

Formula I

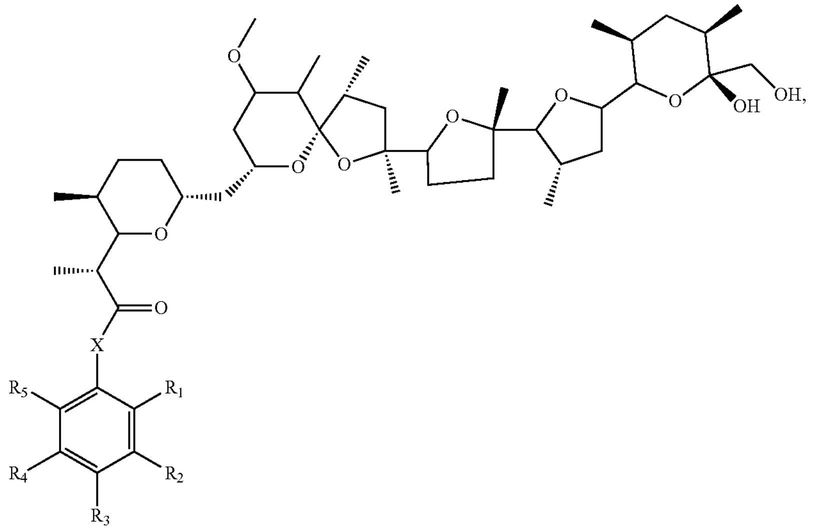

wherein,

X is selected from O or N;

$R_1$, $R_2$, $R_3$, $R_4$ and $R_5$ are same or different and are independently selected from hydrogen, $C_{5-10}$ aryl, halogen or $C_{1-10}$ alkoxy.

The present disclosure further relates to a process for synthesizing the compound of formula I comprising the steps of:

a) dissolving nigericin in dichloromethane;

b) reacting the dissolved nigericin with thionyl chloride; and c) reacting the product of step (b) with an aromatic substituted compound in triethylamine to obtain a compound of formula (I).

The present disclosure further relates to a pharmaceutical composition comprising the compound of formula I, wherein said composition acts an anti bacterial agent or as an anti viral agent.

The present disclosure further provides a method of treating a viral infection comprising providing nigericin or a compound of formula I. The method of treatment of a viral infection may comprise providing a pharmaceutical composition of nigericin or a compound of formula I alone or in combination with a second anti viral agent, a bacterial agent, an anti-microbial agent, an anti-inflammatory agent, an anti-pyretic agent, an anti-malarial agent, an antibiotic, an immune suppressant, an immune booster, an anthelmintic, an analgesic and such like.

The present disclosure also relates to a use of nigericin or a compound of formula I to manufacture a pharmaceutical composition to treat viral infections is provided. The use of nigericin to treat a viral infection may comprise manufacturing a pharmaceutical composition of nigericin or a compound of formula I alone or in combination with a second anti viral agent, a bacterial agent, an anti microbial agent, an anti-inflammatory agent, an anti-pyretic agent, an anti-malarial agent, an antibiotic, an immune suppressant, an immune booster, an anthelmintic, an analgesic and such like.

These and other features, aspects, and advantages of the present subject matter will become better understood with reference to the following description. This summary is provided to introduce a selection of concepts in a simplified form. This summary is not intended to identify key features or essential features of the disclosure, nor is it intended to be used to limit the scope of the subject matter.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 3(*a*) depicts to cell viability of Nigericin and new compounds (N-3 and N-5) with a control DASNCL-29 after 2 h of drug treatment. FIG. 3(*b*) depicts to cell viability of Nigericin and new compounds (N-3 and N-5) with a control DASNCL-29 after 24 h of drug treatment.

Top and bottom left: 2D interaction plots of Nigericin and Remdisvir with RdRp residues. Top and bottom right: Molecular view (3D) of Nigericin and Remdisvir docked on RdRp. The pink spheres show evolutionally conserved regions of the protein.

Figure 5:
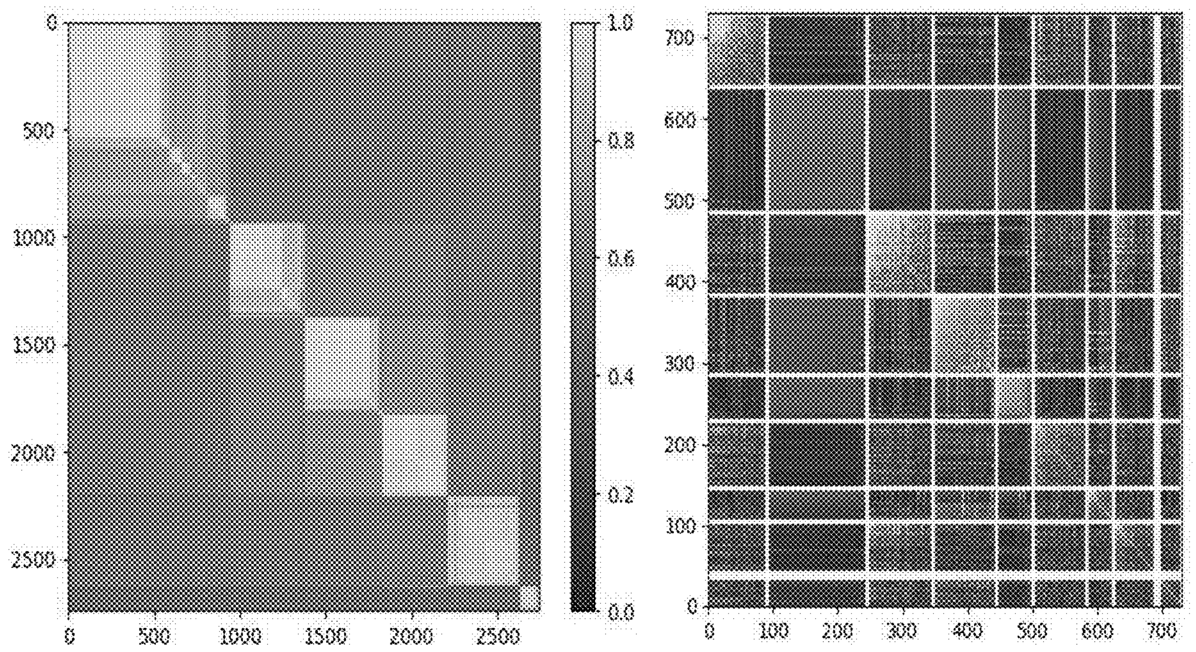

FIG. 5: depicts the glide ligand docking module.

Left image: Clustering of RdRp sequences based on Specification curve analysis (SCA). Right image: Conserved segments of RdRp. For this Specification curve analysis we used residues from 50 to 780.

DETAILED DESCRIPTION OF THE INVENTION

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

Source of Biological Materials:

*S. aureus* (ATCC 9144)

*E. coli* (ATCC 8739)

Wild type Mouse fibroblast cell lines; cell line was received from collaborator as a gift. *Streptomyces* sp. DASNCL-29 is isolated from soil which was collected from Unkeshwar, Maharashtra (GPS: 20°05'57.8" N 78°20'17.4"E).

Deposition details: *Streptomyces* sp. DASNCL-29 has been deposited at the National Center for Microbial Resource, India and has been assigned the accession number: MCC 0151.

The terms N-1, N-2, N-3, N-4 and N-5 are used synonymously for new molecules.

In line with the above objectives, the present invention provides a compound of general formula I,

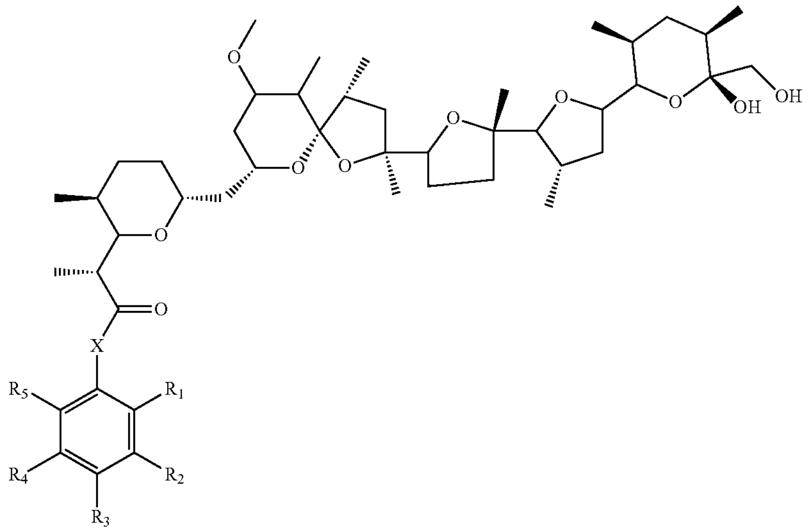

wherein,

X is O or N;

$R_1$, $R_2$, $R_3$, $R_4$ and $R_5$ are same or different and are independently selected from hydrogen, $C_{5-10}$ aryl, halogen, or $C_{1-10}$ alkoxy.

In a preferred embodiment the alkoxy group on either of $R_1$, $R_2$, $R_3$, $R_4$ and $R_5$ is —$OCH_3$.

In another preferred embodiment, the halogen is fluorine.

In a more preferred embodiment, the compound of formula I is selected from:

N-1

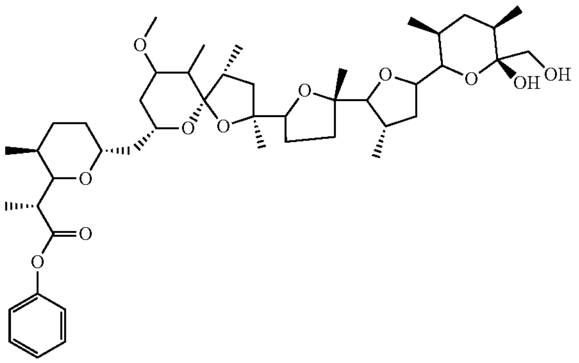

N-2

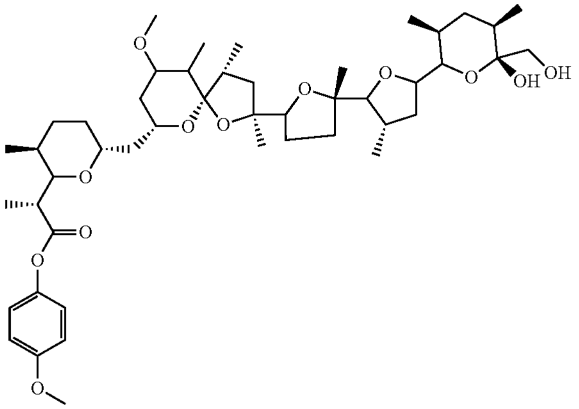

N-3

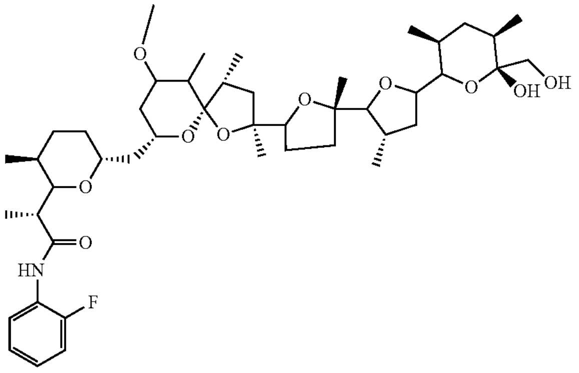

-continued

N-4

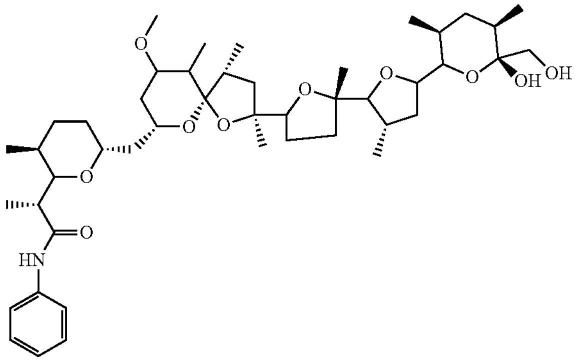

N-5

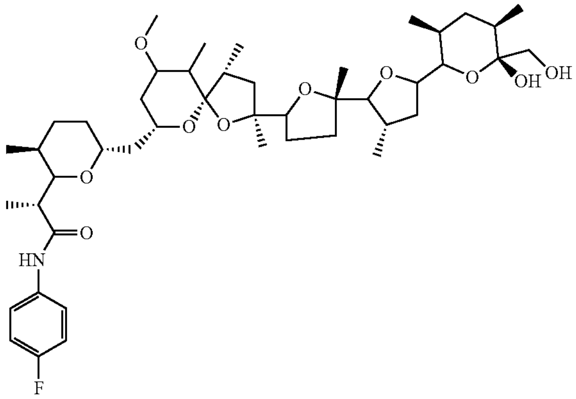

According to an embodiment, the present disclosure provides a compound of Formula I, wherein the compound has an IC50 value greater than 50 μM.

In an embodiment, the present disclosure provides a compound of Formula I, wherein the compounds inhibit both bacteria and viruses. The bacteria includes both gram-positive bacteria and gram-negative bacteria.

In an embodiment, the present disclosure provides a compound of Formula I, wherein the compounds inhibit gram-negative bacteria with a minimum inhibitory concentration (MIC) of less than 0.5 μM.

In one more embodiment, the present disclosure provides a pharmaceutical composition comprising the compound the compound of formula (I) and a pharmaceutically acceptable ingredient, wherein the composition acts as an anti-bacterial agent or as an antiviral agent.

In a further embodiment, the present disclosure provides a process for the preparation of the compound of the general formula (I),

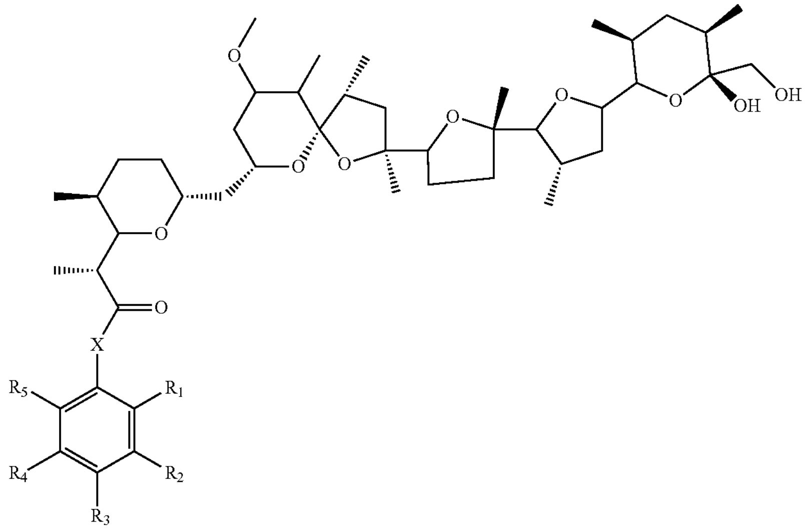

wherein,

X is O or N; and $R_1$, $R_2$, $R_3$, $R_4$ and $R_5$ are same or different independently selected from hydrogen, $C_{5-10}$ aryl, halogen, or $C_{1-10}$ alkoxy.

comprising the steps of:

d) dissolving nigericin in dichloromethane;

e) reacting the dissolved nigericin with thionyl chloride; and f) reacting the product of step (b) with an aromatic substituted compound in triethylamine to obtain a compound of formula (I).

In another embodiment, the present disclosure provides a process for the synthesizing compounds of formula I comprising the steps of:

a. dissolving nigericin in dichloro methane and reacting with thionyl chloride at 50° C. for 6 hours; and b. reacting product of step (a) with an aromatic substituted amine or alcohol in tri ethyl amine for 12 hours to arrive at the desired product of formula I.

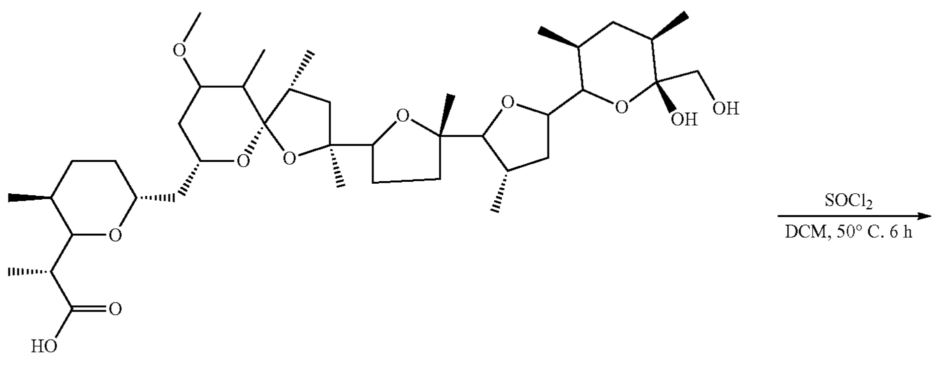

-continued

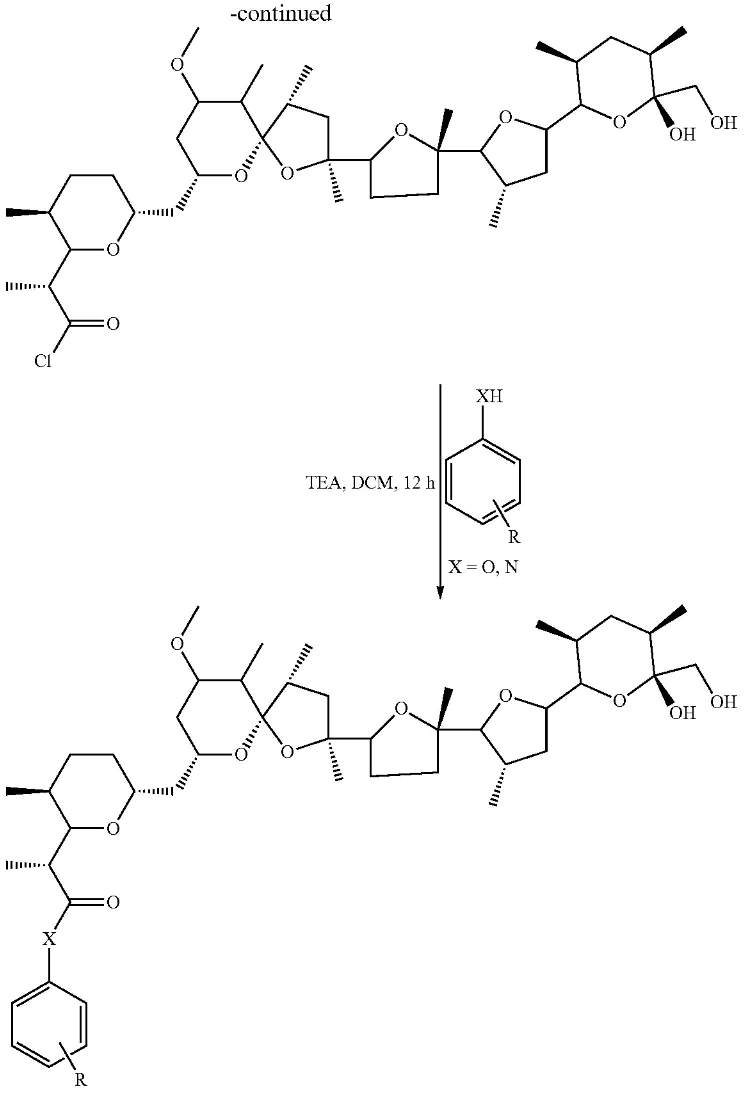

Scheme 1: Reaction Scheme for Fluorination to Obtain Novel Compounds

In an embodiment, the alcohols employed for the synthesis of compound of formula I are phenol or 4-methoxyphenol. In another embodiment, the amines employed for the synthesis of compound of formula I are primary amines selected from aniline, 2-fluroaniline or 4-flouroaniline.

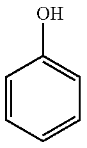
phenol

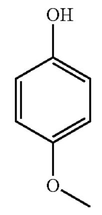
4-methoxyphenol

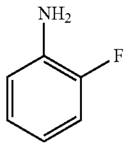
2-fluoroaniline

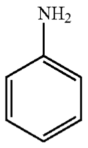
aniline

-continued

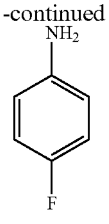
4-fluoroaniline

In an embodiment, the compounds are characterized and their structures elucidated by proton and $^{13}C$ NMR.

Figure 1:
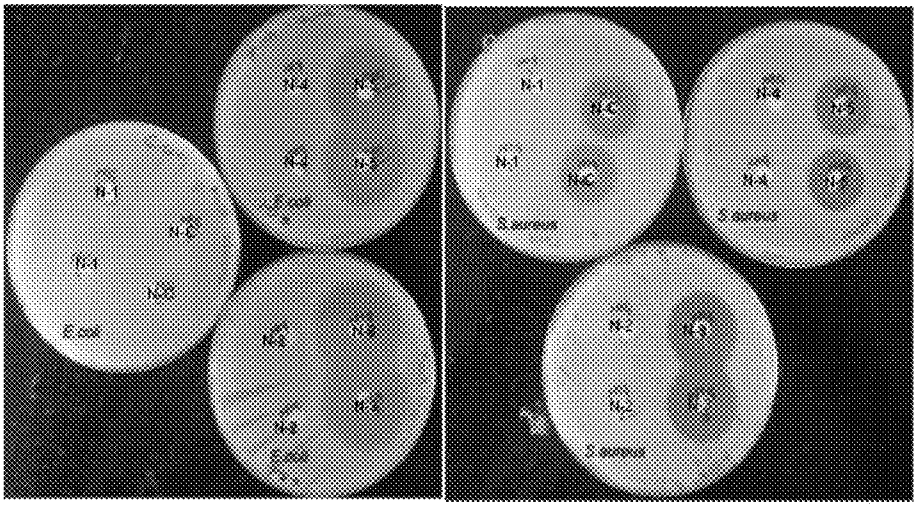
FIG. 1: depicts antibacterial activity of nigericin (N-C) and novel compounds (N1-5 represented as N1-5 respectively) tested against Gram positive (*S. aureus*) test organism by spread plate-disc diffusion method.

In an embodiment, the antibacterial activity of nigericin and compounds of formula I are determined by the Disc diffusion method. FIG. 1 shows the zone of inhibition of the compounds when incubated with gram-positive bacteria and gram-negative bacteria. The compounds of formula I are found to be inhibiting both gram-positive and gram-negative bacteria.

Figure 2:
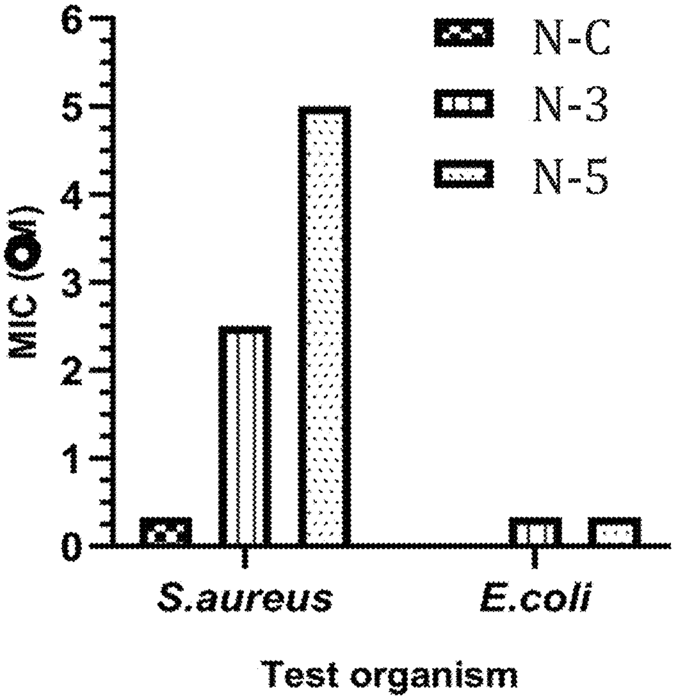
FIG. 2: depicts minimum inhibitory concentration (MIC) of nigericin (N-C) and novel compounds (N-3 and N-5) against Gram-positive bacteria (*S. aureus*) and Gram-negative bacteria (*E. coli*).

FIG. 2 shows the Minimum Inhibitory Concentration (MIC) of nigericin and compounds against bacteria. Nigericin inhibited the growth of gram-positive bacteria *S.*

*aureus* with MIC 0.3 μM, but did not show any inhibition of gram negative organism. In an embodiment, the compounds N-3 and N-5 of formula I inhibit gram-positive bacteria with a Minimum Inhibitory Concentration (MIC) of 2.5 μM and 5 μM respectively. In another preferred embodiment, the compounds N-3 and N-5 of formula I inhibit gram-negative bacteria with a Minimum Inhibitory Concentration of 0.3 μM.

Figure 3A:
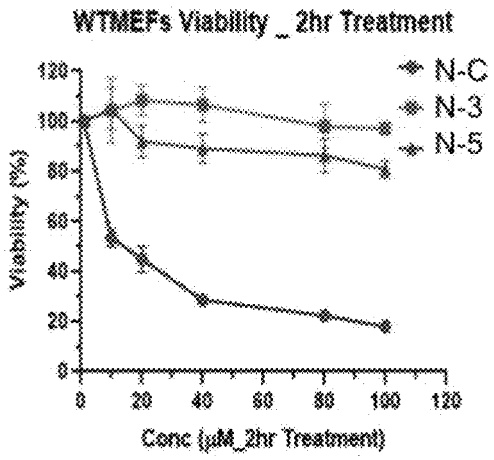
FIG. 3: depicts cytotoxicity of Nigericin (DAS29) and new compounds (N-3 and N-5) on Wild type mouse embryonic fibroblast cell line (WTMEFs) in various concentrations ranging from 100, 80, 40, 20, 10, 1 μM using MTT assay. All drug concentration was taken in triplicate (n=3).
Figure 3B:
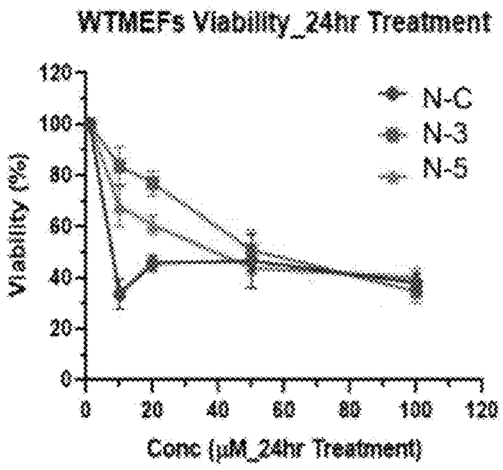

In a preferred embodiment, nigericin and compounds of formula I are tested for toxicity on Wild type mouse fibroblast cell lines using 3-(4,5-dimethylthiazol-2-yl)-2,5-diphenyltetrazolium bromide assay (MTT assay). FIG. 3 shows that nigericin exhibit an IC50 of ~10 mM in 2 h and 24 h treatment. The IC50 for the novel compounds N-3 and N-5 were higher than 100 mM (highest treated concentration) for 2 h treatment, and it is 66.87 and 59.76 mM for 24 h treatment, respectively.

Figure 4:
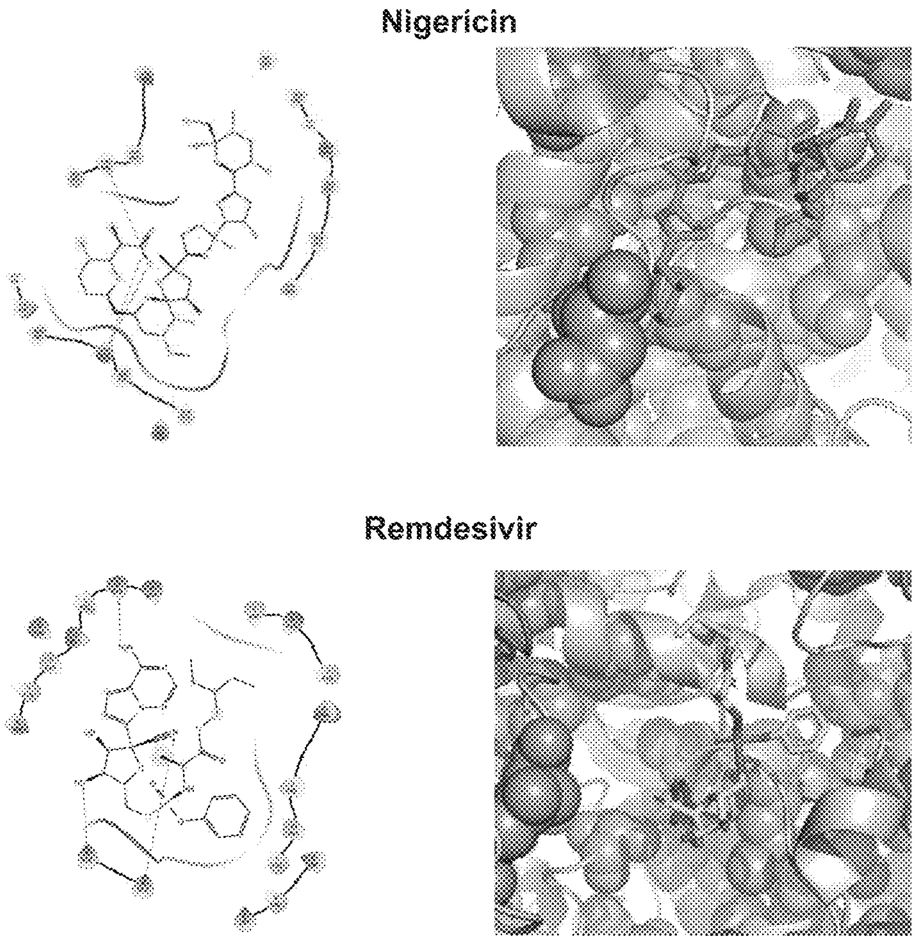
FIG. 4: depicts the interaction of Nigericin and compound of formula I along with Remdisvir for RdRp residues.

In a comparative embodiment, the compound of formula I is found to possess anti-viral activity. FIGS. 4 and 5 shows that, the compounds of formula I is found to be active against SARs CoV2 virus causing Covid-19, refer Table 3. Nigericin and compound of formula I possess anti-viral activity, specifically against SARS Co-V2 virus in comparison with agents known in the art.

Docking Studies for Anti-Viral Activity:

Protein Target and Ligand Preparation

The crystalline structure of the Main protease (PDB ID 6Y84) and RDRP (PDB ID 7BV1; doi.org/10.1101/2020.04.08.032763) was taken from Protein Data Bank Database (PDB). Nigericin and compounds of formula I were designed by using ChemDraw and saved as isomeric SMILEs. Isomeric SMILES were further converted into PDB format using open Babel software. In this study, the inventors have also included various standard drugs which are known to have antiviral activity.

The molecular interaction of Spike protein, main protease Mpro (NC_045512), and RdRp/nsp12 (GenBank: MN908947) with Nigericin and compound of formula I was predicted using Glide software. The ligand coordinates were obtained using open Babel software. In the first step, ligands were prepared using the LigPrep module which produces a low-energy, single 3D structure with correct chiralities. Further, the protein was checked for missing hydrogen atoms incorrect bond, and charge states of various groups using protein preparation wizard. The prepared protein structure was used for grid box generation using the receptor grid generation module. Ligands were docked to the protein by using the Glide ligand docking module. The extra precision (XP) model was used for docking. The docked ligand conformations were evaluated based on docking score, XP gscore, and glide energy. The docking results showed that amongst the targets chosen (Spike protein, Mpro, and RdRp), Nigericin binds well with RdRp. It sits in the RNA binding pocket and thus perhaps blocks the RNA replication. This protein is a key member of the virus RNA replication complex. The results are in line with the experimental observation which suggests that in the case of HIV and Polio Virus, Nigericin inhibits viral RNA synthesis with an effective concentration of (EC50) of ~1 μM. To further evaluate the binding efficacy of Nigericin with reference to other known inhibitors of RdRp, inventors performed similar docking studies of the known inhibitors on coronavirus RdRp. Table 3 shows that in terms of glide energy Nigericin performs better than many well-known anti-viral agents, including Remdesivir, which is currently under clinical trials for COVID-19.

Further, many of the anti-viral agents show differential affinity due to the occurrence of rapid mutations. Therefore, it is imperative to find an inhibitor that binds to a relatively highly conserved location of the protein and yet exhibits higher inhibitory potency. Hence to determine the conserved segments of RdRp, which have remained evolutionarily invariant, inventors performed statistical coupling analysis. This methodology has been successfully demonstrated to delineate the conserved segments of the protein that are functionally important (Cell, 2009 138(4): 774-786). Inventors used 5000 RdRp sequences from the coronavirus family, including recent variants of the virus that causes Covid-19, to analyze the conserved segments of the protein. The analysis shows that Nigericin binds to a segment of the catalytic pocket, which is comprising of 3 evolutionarily conserved regions. In comparison, Remsdivir, a well-known RdRp inhibitor, binds at a place that has just one conserved patch. These results pertaining to RdRp are experimentally verified.

In an embodiment, the present disclosure provides a pharmaceutical composition comprising nigericin, wherein said composition is used acts as an anti-viral agent, alone or in combination with a second anti viral agent, a bacterial agent, an anti microbial agent, an anti-inflammatory agent, an anti-pyretic agent, an anti-malarial agent, an antibiotic, an immune suppressant, an immune booster, an anthelmintic or an analgesic.

In an embodiment, the invention provides a pharmaceutical composition comprising compounds of formula I or its salts, analogues, derivatives, or isomers along with pharmaceutically acceptable ingredients. The composition is selected from oral dosage forms such as tablets, capsules, powder, granules, and such like novel drug delivery systems such as sustained, delayed, extended, timed, or pulsatile release dosage forms, or is administered by the parenteral route and comprises compounds of formula I in a suitable dose. In another embodiment, the invention further discloses a method of treating a subject in need of anti-viral therapy with a composition comprising compounds of formula I.

In a preferred embodiment, the invention provides a composition and a method of treating a subject in need of treatment against viral infection caused by the SARS-nCoV-2 virus. In another embodiment, a method of treating a subject in need of anti-bacterial therapy with a composition comprising a compound of formula I is disclosed. In yet another embodiment, the composition comprising compounds of formula I further comprise one or more drugs selected from, but not limited to anti-viral, anti-bacterial, antibiotic, immune booster, immune suppressant, anti-malarial, anthelmintic, and such like.

The present disclosure further provides a method of treating a viral infection comprising providing nigericin or a compound of formula I. The method of treatment of a viral infection may comprise providing a pharmaceutical composition of nigericin or a compound of formula I alone or in combination with a second anti viral agent, a bacterial agent, an anti microbial gent, an anti-inflammatory agent, an anti-pyretic agnet, an anti-malarial agent, an antibiotic, an immune suppressant, an immune booster, an anthelmintic, an analgesic.

In a further embodiment, the present disclosure provides a method of treating a bacterial infection comprising administering a compound of formula I alone or in combination with a second anti-bacterial agent, an anti viral agent, an anti microbial agent, an anti-inflammatory agent, an anti-pyretic agent, an anti-malarial agent, an antibiotic, an immune suppressant, an immune booster, an anthelmintic or an analgesic.

In yet another embodiment, the present disclosure provides use of nigericin or compound of formula I for the manufacture of a medicament for the treatment of a viral infection. It further provides use of nigericin or a compound of formula I to manufacture a pharmaceutical composition to treat viral infections is provided. The use of nigericin to treat a viral infection may comprise providing a pharmaceutical composition of nigericin or a compound of formula I alone or in combination with a second anti viral agent, a bacterial agent, an anti microbial agent, an anti-inflammatory agent, an anti-pyretic agent, an anti-malarial agent, an antibiotic, an immune suppressant, an immune booster, an anthelmintic, and an analgesic.

EXAMPLES

The following examples, which include preferred embodiments, will serve to illustrate the practice of this invention, it being understood that the particulars shown are by way of example and for purpose of illustrative discussion of preferred embodiments of the invention.

Example: 1

Synthesis of Compounds of Formula I

Nigericin used is obtained from indigenously isolated *Streptomyces* sp. Strain DASNCL-29.

Step-I

Nigericin (1 mmol) and Thionyl chloride (3 mmol) were refluxed (50° C.) in Dichloromethane for 6 h.

Step-II

Amine or alcohol as specified above (1 mmol) and triethyl amine (3 mmol) were added in Step-I and stirred for 12 h to obtain the desired product.

Example 2

NMR Based Characterization of Analog 1-5 (N1-5)

NMR Based Characterization of Analog 1 (N-1)

N-1

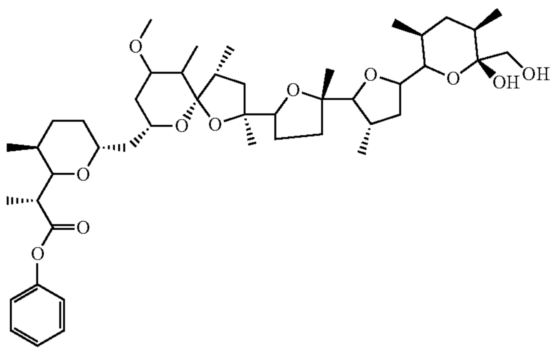

phenyl (2R)-2-((3S,6R)-6-(((2S,4R,5R,7R)-2-((2S,3'S)-5'-((3S,5R,6R)-6-hydroxy-6-(hydroxymethyl)-3,5-dimethyltetrahydro-2H-pyran-2-yl)-2,3'-dimethyloctahydro-[2,2'-bifuran]-5-yl)-9-methoxy-2,4,10-trimethyl-1,6-dioxaspiro[4.5]decan-7-yl)methyl)-3-methyltetrahydro-2H-pyran-2-yl)propanoate $^1$H NMR (400 MHz, CHLOROFORM-d) 7.24 (m, 2H) 6.91 (m, 1H), 6.84 (dd, 8.1, 2.2 Hz 2H), 4.42-4.29 (m, 1H), 4.21-3.91 (m, 5H), 3.77 (d, J=10.4 Hz, 1H), 3.58-3.44 (m, 3H), 3.35 (s, 3H), 2.57-2.43 (m, 1H), 2.40-2.10 (m, 5H), 2.09-2.00 (m, 3H), 1.96 (d, J=15.9 Hz, 1H), 1.87-1.72 (m, 4H), 1.72-1.54 (m, 3H), 1.51-1.22 (m, 11H), 1.19-1.07 (m, 5H), 1.04 (dd, J=7.0, 11.9 Hz, 7H), 0.98-0.79 (m, 15H) $^{13}$C NMR (101 MHz, CDCl3) 177.4, 160.6. 130.4, 121.3, 116.7, 108.2, 97.0, 85.8, 83.4, 82.4, 81.5, 78.0, 77.2, 74.4, 72.9, 69.0, 68.3, 60.3, 60.2, 57.4, 44.2, 42.5, 38.9, 37.4, 37.1, 35.7, 35.3, 35.1, 32.5, 32.2, 31.7, 30.7, 27.9, 27.5, 26.0, 25.7, 23.4, 22.6, 17.3, 16.3, 15.6, 14.2, 13.2, 13.1, 13.0, 10.8

NMR Based Characterization of Analog 2 (N-2)

N-2

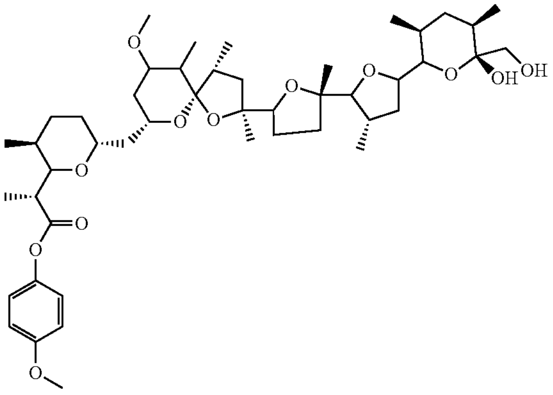

$^1$H NMR (400 MHz, CHLOROFORM-d) 7.1 (d, J=8.1 2H) 6.5 (d, J=8.1 2H), 4.42-4.29 (m, 1H), 4.20-3.91 (m, 5H), 3.82 (d, J=10.4 Hz, 1H), 3.58-3.44 (m, 3H), 3.35 (s, 3H), 2.57-2.43 (m, 1H), 2.40-2.10 (m, 5H), 2.09-2.00 (m, 3H), 1.96 (d, J=15.9 Hz, 1H), 1.87-1.72 (m, 4H), 1.72-1.54 (m, 3H), 1.51-1.22 (m, 11H), 1.19-1.07 (m, 5H), 1.04 (dd, J=7.0, 11.9 Hz, 7H), 0.98-0.79 (m, 15H) $^{13}$C NMR (101 MHz, CDCl3) 177.4, 160.6. 130.4, 121.3, 116.7, 108.2, 97.0, 85.8, 83.4, 82.4, 81.6, 78.6, 77.6, 74.4, 72.6, 69.0, 68.7, 60.3, 60.2, 57.4, 44.2, 42.5, 38.59, 37.4, 37.5, 35.6, 35.8, 35.6, 32.6, 32.8, 31.6, 30.6, 27.7, 27.7, 26.0, 25.7, 23.4, 22.6, 17.3, 16.4, 15.4, 14.7, 13.6, 13.5, 13.3, 10.4

NMR Based Characterization of Analog 3 (N-3)

N-3

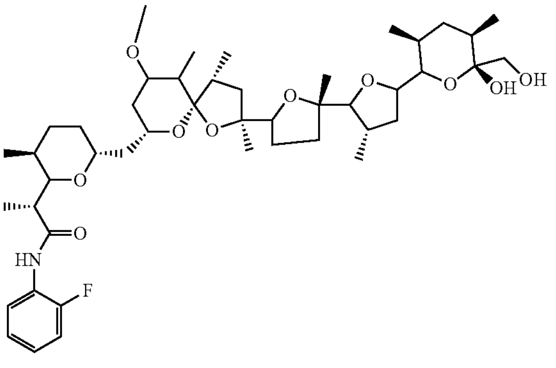

(2R)—N-(2-fluorophenyl)-2-((3S,6R)-6-(((2S,4R,5R,7R)-2-((2S,3'S)-5'-((3S,5R,6R)-6-hydroxy-6-(hydroxymethyl)-3,5-dimethyltetrahydro-2H-pyran-2-yl)-2,3'-dimethyloctahydro-[2,2'-bifuran]-5-yl)-9-methoxy-2,4,10-trimethyl-1,6-dioxaspiro[4.5]decan-7-yl)methyl)-3-methyltetrahydro-2H-pyran-2-yl) propanamide $^1$H NMR (400 MHz, CHLOROFORM-d) 7.33 (m 2H) 7.2 (m, 3H), 4.41-4.23 (m, 1H), 4.21-3.95 (m, 5H), 3.84 (d, J=10.4 Hz, 1H), 3.54-3.43 (m, 3H), 3.36 (s, 3H), 2.54-2.43 (m, 1H), 2.43-2.11 (m, 5H), 2.06-2.01 (m, 3H), 1.96 (d, J=15.9 Hz, 1H), 1.87-1.72 (m, 4H), 1.72-1.54 (m, 3H), 1.51-1.22 (m, 11H), 1.19-1.07 (m, 5H), 1.04 (dd, J=7.0, 11.9 Hz, 7H), 0.98-0.79 (m, 15H) $^{13}$C NMR (101 MHz, CDCl3) 174.4, 158.5 (d, J=164 Hz), 160.6. 130.3 (d, J=10.3 Hz), 121.4, 116.5 (d, J=19.2 Hz), 108.5, 97.0, 85.7, 83.6, 82.7, 81.4, 78.8, 77.5, 74.6, 72.4, 69.0, 68.4, 61.3, 61.4, 57.4, 44.4, 42.5, 38.4, 37.4, 37.1, 35.7, 35.6, 35.3, 32.2, 32.1, 31.1, 30.7, 27.9, 27.5, 26.0, 25.3, 23.3, 22.5, 17.5, 16.4, 15.4, 14.4, 14.2, 13.6, 13.4, 10.3

NMR Based Characterization of Analog 4 (N-4)

N-4

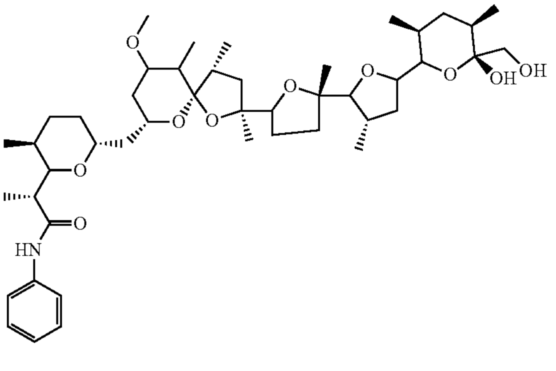

phenyl (2R)-2-((3S,6R)-6-(((2S,4R,5R,7R)-2-((2S,3'S)-5'-((3S,5R,6R)-6-hydroxy-6-(hydroxymethyl)-3,5-dimethyltetrahydro-2H-pyran-2-yl)-2,3'-dimethyloctahydro-[2,2'-bifuran]-5-yl)-9-methoxy-2,4,10-trimethyl-1,6-dioxaspiro[4.5]decan-7-yl)methyl)-3-methyltetrahydro-2H-pyran-2-yl)propanoate $^1$H NMR (400 MHz, CHLOROFORM-d) 7.33 (m, 2H) 70 (m, 1H), 6.88 (dd, 8.1, 2.2 Hz 2H), 4.42-4.29 (m, 1H), 4.24-3.95 (m, 5H), 3.75 (d, J=10.4 Hz, 1H), 3.55-3.44 (m, 3H), 3.35 (s, 3H), 2.54-2.44 (m, 1H), 2.40-2.14 (m, 5H), 2.1-2.00 (m, 3H), 1.96 (d, J=15.9 Hz, 1H), 1.86-1.74 (m, 4H), 1.72-1.55 (m, 3H), 1.51-1.22 (m, 11H), 1.19-1.06 (m, 5H), 1.05 (dd, J=7.0, 11.9 Hz, 7H), 0.98-0.79 (m, 15H); $^{13}$C NMR (101 MHz, CDCl3) 175.4, 160.6. 130.4, 121.3, 116.7, 108.2, 97.0, 85.8, 83.4, 82.4, 81.5, 78.0, 77.2, 74.4, 72.9, 69.0, 68.3, 60.3, 60.2, 57.8, 44.8, 42.5, 38.9, 37.8, 37.2, 35.7, 35.7, 35.0, 32.9, 32.2, 31.4, 30.4, 27.8, 27.7, 26.0, 25.8, 23.7, 22.7, 17.7, 16.7, 15.7, 14.2, 13.9, 13.7, 13.3, 10.5

NMR Based Characterization of Analog 5 (N-5)

N-5

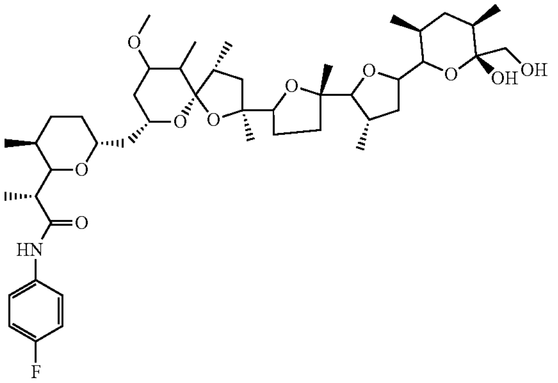

$^1$H NMR (400 MHz, CHLOROFORM-d) 7.35 (m 2H) 7.5 (m, 1H), 4.42-4.25 (m, 1H), 4.24-3.96 (m, 5H), 3.82 (d, J=10.4 Hz, 1H), 3.52-3.43 (m, 3H), 3.36 (s, 3H), 2.53-2.43 (m, 1H), 2.43-2.17 (m, 5H), 2.076-2.03 (m, 3H), 1.98 (d, J=15.9 Hz, 1H), 1.87-1.72 (m, 4H), 1.74-1.53 (m, 3H), 1.51-1.21 (m, 11H), 1.19-1.07 (m, 5H), 1.04 (dd, J=7.0, 11.9 Hz, 7H), 0.98-0.79 (m, 15H) $^{13}$C NMR (101 MHz, CDCl3) 174.4, 161.5 (d, J=165.3 Hz), 160.6. 131.2 (d, J=8.9 Hz), 121.4, 116.5 (d, J=19.2 Hz), 97.1, 85.5, 83.6, 82.3, 81.2, 78.5, 77.6, 74.4, 72.4, 69.1, 68.2, 61.2, 61.5, 57.7, 44.7, 42.8, 38.4, 37.7, 37.1, 35.5, 35.7, 35.6, 32.1, 32.1, 31.5, 30.7, 27.9, 27.5, 26.0, 25.3, 23.3, 22.5, 17.5, 16.4, 15.4, 14.4, 14.2, 13.6, 13.4, 10.3.

Example 3

Antibacterial Activity Screening:

Disc Diffusion Method:

Nigericin along with compounds of formula I were tested against Gram-positive (*S. aureus*) and Gram-negative (*E. coli*) test organisms by spread plate-disc diffusion method. 20 μl from 1 mg/ml concentration stock was used per disc for each test compound and plated were incubated at 37° C. for 24 h. After the incubation period zone of inhibition was measured.

MIC determination: Minimum inhibitory concentration was determined using micro-dilution method in the 96 well plates. 20 μl from 1 mg/ml stock was mixed with culture to get 66 μg/ml concentration and serially diluted in further well to get a concentration of 33 μg/ml, 16.5 μg/ml and so on, refer FIG. 1.

Results:

Antibacterial Activity (Disc Diffusion Method)

TABLE 1

Antibacterial activity by disc diffusion method. (Zone measured in mm)

| | N-C | N-1 | N-2 | N-3 | N-4 | N-5 |
|---|---|---|---|---|---|---|
| *S. aureus* | 22 | 0 | 0 | 31 | 0 | 23 |
| *E. coli* | 0 | 0 | 0 | 33 | 0 | 30 |

"0" indicates no antibacterial activity

Results of Minimum inhibitory concentration (MIC) determination showed that the Nigericin inhibited the growth of *S. aureus* with MIC 0.3 μM, whereas fluorinated compound N-3 and N-5 showed a MIC value of 2.5 μM and 5 μM respectively. In the case of Gram-negative organism (*E. coli*), Nigericin did not show any inhibition however N-3 and N-5 both showed MIC value of 0.3 μM, refer FIG. 2.

Example 4

In-Vitro Toxicity:

Wild-type mouse fibroblast cell line (WTMEFs) was used to assess the toxicity associated with nigericin and its fluorinated analogues for the viability using 3-(4,5-dimethylthiazol-2-yl)-2,5-diphenyltetrazolium bromide assay (MTT assay). WTMEFs cell line was seeded in 96-well plates at a density of 5000 cells per well in 100 ml DMEM media containing 10% FBS. The cell lines were incubated for 24 h in a $CO_2$ incubator at 37° C. After 24 h, the drug was added at a concentration of 100, 80, 40, 20, 10 and 1.0 mM and incubated for 2 h and 24 h. MTT assay was carried out to verify the cell viability after 2 h and 24 h of drug treatment in respective plates. All drug concentration was used in triplicate (n=3).

Nigericin showed an IC50 of ~10 μM in 2 h and 24 h treatment. However, the IC50 of fluorinated molecule N-3 and N-5 was greater than 100 μM (highest treated concentration) for 2 h treatment and 66.87 μM and 59.76 μM for 24 h treatment with fluorinated molecules respectively, refer FIG. 3.

In the cytotoxicity experiment, nigericin showed an IC50 of ~10 mM in 2 h and 24 h treatment. However, the IC50 for the fluorinated analogues N-3 and N-5 were higher than >100 mM (highest treated concentration) for 2 h treatment, and it was 66.87 and 59.76 mM for 24 h treatment, respectively.

TABLE 2

Cytotoxicity: IC50 of Nigericin, analogue-3(N-n-3) and analogue-5 (N-n-5)

| | | Treatment | |
|---|---|---|---|
| | | 2 h | 24 h |
| $IC_{50}$ (μM) | Nigericin | ~10 | 9.22 |
| | N-3 | >100 | 66.87 |
| | N-5 | >100 | 59.76 |

Example 5

In Silico Docking of Protein and Ligands

The molecular interaction of main protease and RDRP with Nigericin and novel compounds was predicted using Glide software. The ligand coordinates were obtained using open Babel software. In the first step, ligands were prepared using the LigPrep module which produces a low-energy, single 3D structure with correct chiralities. Further, the protein was checked for missing hydrogen atoms incorrect bond, and charge states of various groups using protein preparation wizard. The prepared protein structure was used for grid box generation using the receptor grid generation module. Ligands were docked to the protein by using the Glide ligand docking module. The extra precision (XP) model was used for docking. The docked ligand conformations were evaluated based on docking score, XP gscore, and glide energy.

In Silico Result Interpretation

Nigericin and compounds N 1-5 were docked along with known antiviral drugs to screen their ability to bind at the ligand-binding site of SARS-Cov2 main protease and RDRP. The docking scores and glide energy of the Nigericin and compounds of formula I were compared with the score of known antiviral drugs. The results showed that these molecules exhibit good binding energy ranging from −52.908 to −41.882 kcal/mol in the case of the main protease and −51.599 to −43.952 kcal/mol in the case of RdRP (Table) which can be considered as good targets for SARS-Cov2 main protease and RdRP, refer FIGS. 4 and 5.

TABLE 3

Docking results showing docking and other scores for ligand, when docked on RdRp: -

| Sl. No | Ligand | Docking Score | XP GScore | glide gscore | glide energy |
|---|---|---|---|---|---|
| 1 | Nigericin | −4.834 | −4.835 | −4.835 | −43.952 |
| 2 | Galidesivir | −4.673 | −4.736 | −4.736 | −39.419 |
| 3 | N3 (*Nature* 2020) | −4.485 | −4.485 | −4.485 | −75.946 |
| 4 | Luteolin | −4.262 | −4.302 | −4.302 | −37.645 |
| 5 | Nafamostat | −4.099 | −4.099 | −4.099 | −39.382 |
| 6 | Emodin | −4.023 | −4.117 | −4.117 | −33.702 |
| 7 | Eflornithine | −3.845 | −4.424 | −4.424 | −27.626 |
| 8 | Ribavirin | −3.589 | −3.589 | −3.589 | −40.218 |
| 9 | Gemcitabine | −3.518 | −3.524 | −3.524 | −34.729 |
| 10 | Dasatinib | −3.444 | −3.866 | −3.866 | −50.972 |
| 11 | Hydroxychloroquine | −3.308 | −3.358 | −3.358 | −43.863 |
| 12 | N1 (*Nature* 2020) | −3.251 | −3.251 | −3.251 | −52.367 |
| 13 | Monensin | −3.208 | −3.209 | −3.209 | −43.985 |
| 14 | Mycophenolicacid | −3.093 | −3.124 | −3.124 | −37.924 |
| 15 | N - 4 | −2.751 | −2.751 | −2.751 | −49.727 |
| 16 | Saracatinib | −2.737 | −3.741 | −3.741 | −49.487 |
| 17 | Remdesivir | −2.727 | −2.727 | −2.727 | −57.331 |
| 18 | Rapamycin (Sirolimus) | −2.266 | −2.267 | −2.267 | −56.485 |
| 19 | N - 5 | −2.261 | −2.261 | −2.261 | −50.948 |
| 20 | chloroquin | −2.176 | −2.212 | −2.212 | −28.931 |
| 21 | Amiodarone | −2.038 | −2.058 | −2.058 | −41.671 |
| 22 | Indomethacin | −2.022 | −2.023 | −2.023 | −31.027 |
| 23 | N - 3 | −2.013 | −2.013 | −2.013 | −47.978 |
| 24 | Emetine | −2.004 | −2.011 | −2.011 | −45.339 |
| 25 | Hexachlorophene | −1.999 | −4.521 | −4.521 | −32.715 |
| 26 | Niclosamide | −1.863 | −1.929 | −1.929 | −28.069 |
| 27 | Homoharringtonine | −1.404 | −1.516 | −1.516 | −47.882 |
| 28 | Ritonavir | −1.379 | −1.379 | −1.379 | −63.491 |

TABLE 3-continued

Docking results showing docking and other scores for ligand, when docked on RdRp: -

| Sl. No | Ligand | Docking Score | XP GScore | glide gscore | glide energy |
|---|---|---|---|---|---|
| 29 | Trametinib | −1.271 | −1.271 | −1.271 | −49.720 |
| 30 | N - 1 | −0.754 | −0.754 | −0.754 | −45.150 |
| 31 | Camostat | −0.738 | −0.738 | −0.738 | −44.357 |
| 32 | Promethazine | −0.507 | −0.508 | −0.508 | −29.308 |
| 33 | Lopinavir | 0.128 | 0.128 | 0.128 | −60.755 |
| 34 | Imatinib | 0.146 | −2.358 | −2.358 | −47.161 |
| 35 | Chlorpromazine | 0.340 | 0.339 | 0.339 | −30.448 |
| 36 | ABT-263 | 0.734 | −1.568 | −1.568 | −76.397 |
| 37 | N - 2 | 0.876 | 0.876 | 0.876 | −51.599 |

ADVANTAGES OF THE INVENTION

The present disclosure provides novel compounds with activity against both bacteria including gram negative microorganisms and viruses.

The Chemically derived compounds of the present disclosure are tenfold lesser toxic compared to nigericin.

The present disclosure also provides cost-effective process of preparation, devoid of metal and acids.

We claim:

1. A compound of general formula (I):

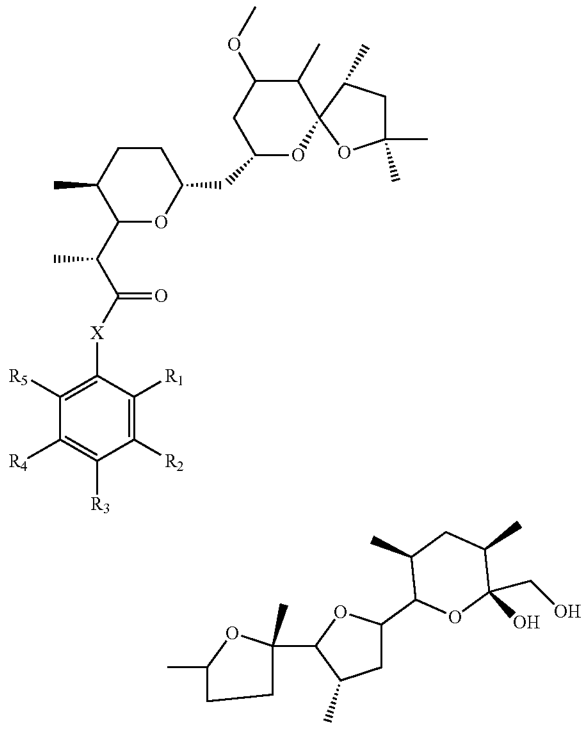

wherein,

X is O or NH; and $R_1$, $R_2$, $R_3$, $R_4$, and $R_5$ are same or different and are independently selected from hydrogen, $C_{5-10}$ aryl, halogen, or $C_{1-10}$ alkoxy.

2. The compound as claimed in claim 1, wherein the alkoxy group is —$OCH_3$, and the halogen is a fluorine.

3. The compound as claimed in claim 1, wherein the compound is:

N-1

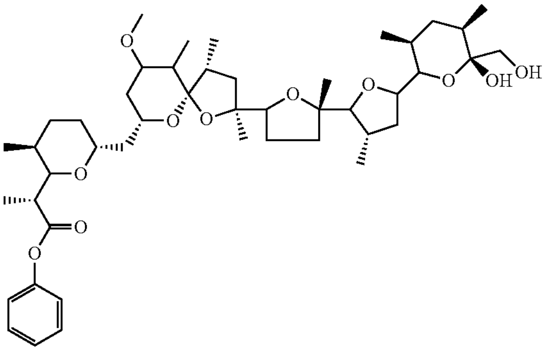

N-2

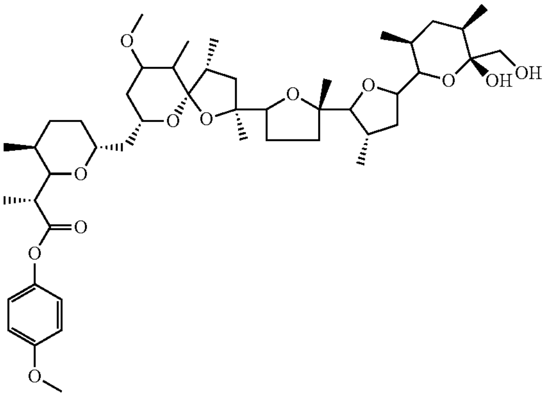

-continued

N-3

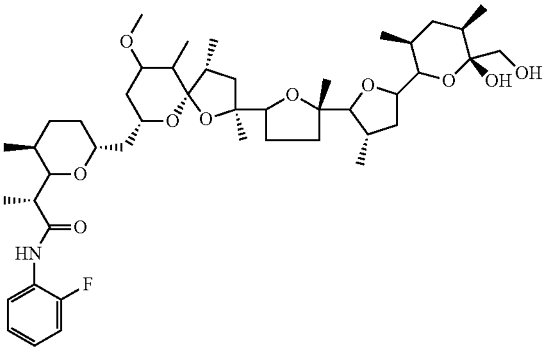

N-4

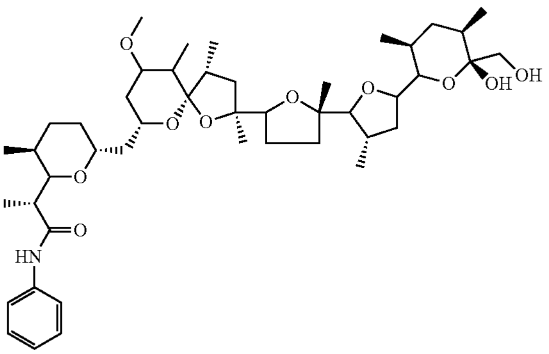

-continued

N-5

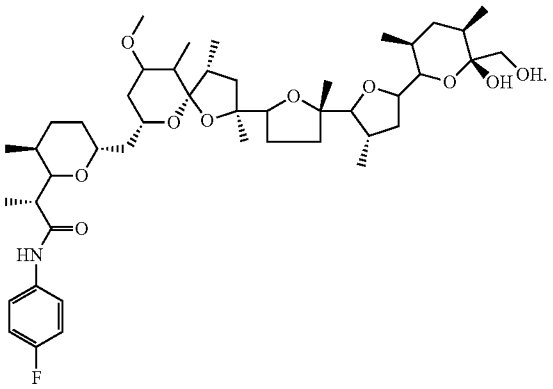

4. The compound as claimed in claim 1, wherein the compound has an IC50 value greater than 50 μM.

5. The compound as claimed in claim 1, wherein the compound inhibits both bacteria, and viruses.

6. The compound as claimed in claim 5, wherein the bacteria consists of gram-positive bacteria and gram-negative bacteria.

7. The compound as claimed in the claim 6, wherein the compound inhibits gram-negative bacteria with a minimum inhibitory concentration (MIC) of less than 0.5 μM.

8. A process for the preparation of the compound of the general formula (I),

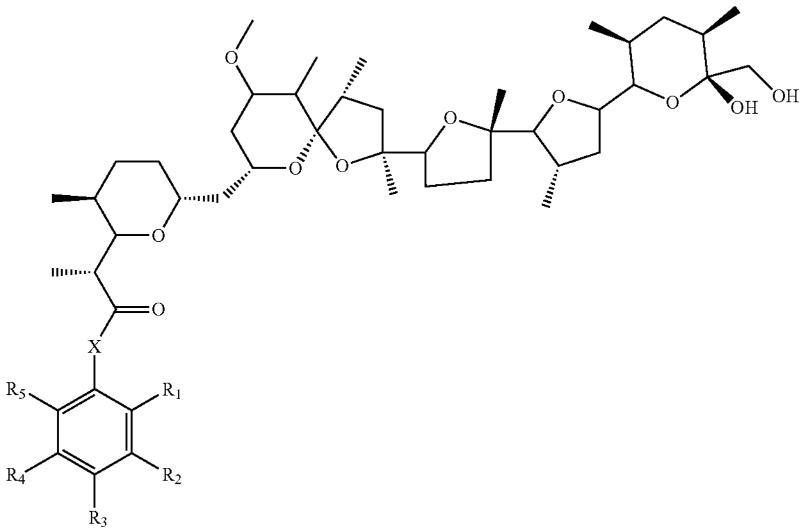

wherein,

X is O or NH; and $R_1$, $R_2$, $R_3$, $R_4$, and $R_5$ are same or different independently selected from hydrogen, $C_{5-10}$ aryl, halogen, or $C_{1-10}$ alkoxy;

comprising the steps of:

a) dissolving nigericin in dichloromethane;

b) reacting the dissolved nigericin with thionyl chloride; and c) reacting the product of step (b) with an aromatic substituted compound of the following formula:

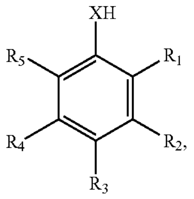

wherein X is O or NH in triethylamine to obtain a compound of formula (I).

9. The process as claimed in claim 8, wherein the aromatic substituted compound is selected from phenol, 4-methoxyphenol, aniline, 2-fluoroaniline, and 4-fluoroaniline.

10. A pharmaceutical composition comprising the compound as claimed in claim 1 in combination with an anti viral agent, a bacterial agent, a second bacterial agent, an anti-inflammatory agent, an anti-pyretic agent, an anti-malarial agent, an antibiotic, an immune suppressant, an immune booster, an anthelmintic, or an analgesic.

11. A method of treating viral or bacterial infections comprising administering an agent selected from the compound of formula I alone or in combination with an anti viral agent, a bacterial agent, a second anti-bacterial agent, an anti-inflammatory agent, an anti-pyretic agent, an anti-malarial agent, an antibiotic, an immune suppressant, an immune booster, an anthelmintic, or an analgesic.

* * * * *